US00PP26620P2

(12) United States Plant Patent
Wood

(10) Patent No.: US PP26,620 P2
(45) Date of Patent: Apr. 19, 2016

(54) ***HYDRANGEA* PLANT NAMED 'SMHPZIND'**

(50) Latin Name: *Hydrangea paniculata*
Varietal Denomination: SMHPZIND

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 101 days.

(21) Appl. No.: 14/120,738

(22) Filed: Jun. 21, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

UPOV hit for *Hydrangea* named 'SMHPZIND', CA PBR 13-8111, publication date Oct. 31, 2013.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'SMHPZIND', characterized by its upright and somewhat outwardly spreading plant habit; strong and sturdy stems; freely flowering habit; inflorescences with sterile flowers that are initially light green in color turning white with maturity and becoming light red purple with subsequent development in the autumn; and good garden performance.

3 Drawing Sheets

Botanical designation: *Hydrangea paniculata.*
Cultivar denomination: 'SMHPZIND'.

BACKGROUND OF THE INVENTION

The present invention relates to a new and distinct *Hydrangea* plant, botanically known as *Hydrangea paniculata* and hereinafter referred to by the name 'SMHPZIND'.

The new *Hydrangea* plant is a product of a planned breeding program conducted by the Inventor in Grand Haven, Mich. The objective of the breeding program was to develop new *Hydrangea* plants with strong stems and large and attractive inflorescences.

The new *Hydrangea* plant originated from an open-pollination in July, 2007 of *Hydrangea paniculata* 'DVP Pinky', disclosed in U.S. Plant Pat. No. 16,166, as the female, or seed parent and an unknown selection of *Hydrangea paniculata* as the male, or pollen, parent. The new *Hydrangea* plant was discovered and selected by the Inventor as a single flowering plant from within the progeny of the stated open-pollination in a controlled environment in Grand Haven, Mich. in July, 2009.

Asexual reproduction of the new *Hydrangea* plant by softwood cuttings in a controlled environment in Grand Haven, Mich. since July, 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHPZIND'. These characteristics in combination distinguish 'SMHPZIND' as a new and distinct *Hydrangea* plant:

1. Upright and somewhat outwardly spreading plant habit.
2. Strong and sturdy stems.
3. Freely flowering habit.
4. Inflorescences with sterile flowers that are initially light green in color turning white with maturity and becoming light red purple with subsequent development in the autumn.
5. Good garden performance.

Plants of the new *Hydrangea* differ from plants of the female parent, 'DVP Pinky', in flowering habit as plants of the new *Hydrangea* have more flowers per inflorescence than plants of 'DVP Pinky'.

Plants of the new *Hydrangea* can be compared to plants of *Hydrangea paniculata* 'SMHPFL', disclosed in U.S. Plant patent application Ser. No. 13/987,719. In side-by-side comparisons, plants of the new *Hydrangea* differed primarily from plants of 'SMHPFL' in the following characteristics:

1. Sterile flowers of plants of the new *Hydrangea* were smaller than sterile flowers of plants of 'SMHPFL'.
2. In the autumn, plants of the new *Hydrangea* had sterile flowers that were light red purple in color whereas plants of 'SMHPFL' had sterile flowers that were red in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMHPZIND' with developing inflorescences.

The photograph on the second sheet is a close-up view of a typical mature inflorescence.

The photograph on the third sheet is a side perspective view of a typical flowering plant of 'SMHPZIND' in the autumn.

DETAILED BOTANICAL DESCRIPTION

Plants used for the aforementioned photographs and the following description were grown during the spring, summer and autumn in three-gallon containers in an outdoor nursery in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea paniculata* 'SMHPZIND'.

Parentage:

*Female, or seed, parent.*—*Hydrangea paniculata* 'DVP Pinky', disclosed in U.S. Plant Pat. No. 16,166.

*Male, or pollen, parent.*—Unknown selection of *Hydrangea paniculata,* not patented.

Propagation:

*Type cutting.*—By softwood cuttings.

*Time to initiate roots, summer.*—About 18 days at temperatures of about 27° C.

*Time to produce a rooted young plant, summer.*—About two months at temperatures of about 27° C.

*Root description.*—Fine and thick; white and brown in color.

*Rooting habit.*—Freely branching; dense.

Plant description:

*Plant form and growth habit.*—Perennial deciduous shrub; upright and somewhat outwardly spreading plant habit; broad inverted triangle; strong and sturdy lateral branches; freely branching habit with about 18 lateral branches developing per plant; vigorous growth habit.

*Plant height.*—About 1 meter.

*Plant diameter or area of spread.*—About 75 cm.

*Lateral branches.*—Length: About 80 cm. Diameter: About 5 mm. Internode length: About 5 cm. Texture: Smooth, glabrous. Strength: Strong, sturdy. Color, developing: Close to 154A. Color, developed: Close to 195A.

Leaf description:

*Arrangement.*—Opposite, simple.

*Length.*—About 11.5 cm.

*Width.*—About 5 cm.

*Shape.*—Ovate.

*Apex.*—Acute.

*Base.*—Acute to rounded.

*Margin.*—Serrulate.

*Texture, upper surface.*—Slightly pubescent.

*Texture, lower surface.*—Smooth; glabrous.

*Venation pattern.*—Pinnate.

*Color.*—Developing leaves, upper and lower surfaces: Close to 146B. Fully expanded leaves, upper surface: Close to 137A; venation, close to 146B. Fully expanded leaves, lower surface: Close to 137A; venation, close to 146D.

*Petioles.*—Length: About 1.5 cm. Diameter: About 2 mm. Texture, upper and lower surfaces: Smooth, glabrous. Color, upper and lower surfaces: Close to 146A.

Inflorescence & flower description:

*Flower type and habit.*—Single sterile and fertile flowers arranged on large terminal panicles; fertile flowers face upright and sterile flowers face upright to outwardly.

*Fragrance.*—None detected.

*Natural flowering season.*—Continuous flowering throughout the summer into the autumn Grand Haven, Mich.

*Quantity of flowers.*—Freely flowering habit; about 700 fertile flowers and about 960 sterile flowers per inflorescence.

*Inflorescence height.*—About 20 cm.

*Inflorescence diameter.*—About 18 cm.

*Flower diameter, fertile flowers.*—About 2 mm to 3 mm.

*Flower depth (height), fertile flowers.*—About 1 mm to 2 mm.

*Flower diameter, sterile flowers.*—About 3 cm.

*Flower depth (height), sterile flowers.*—About 3 mm.

*Flower buds, fertile and sterile flowers.*—Length: About 2 mm. Diameter: About 1 mm. Shape: Ovoid. Color: Close to 154D.

*Petals, fertile flowers only.*—Arrangement: Five in a single whorl. Length: About 3 mm. Width: About 2 mm. Shape: Ovate. Apex: Acute. Base: Cuneate. Margin: Entire. Texture, upper and lower surfaces: Smooth, glabrous. Color: When opening, upper surface: Close to 157A. When opening, lower surface: Close to 157C. Fully opened, upper and lower surfaces: Close to 157B.

*Sepals, fertile flowers.*—None observed.

*Sepals, sterile flowers.*—Quantity per flower: Four in a single whorl. Length: About 1.4 cm. Width: About 1.1 cm. Shape: Elliptical to obovate. Apex: Acute to obtuse. Base: Obtuse. Margin: Entire. Texture, upper and lower surfaces: Smooth, glabrous. Color: When opening, upper and lower surfaces: Close to 150D. Fully opened, upper and lower surfaces: Close to 155D; in the autumn, color becoming progressively closer to 58B.

*Pedicels, fertile flowers.*—Angle: Erect to about 30° from inflorescence axis. Strength: Strong, sturdy. Length: About 1 mm. Diameter: About 1 mm. Texture: Smooth, glabrous. Color: Close to 145D.

*Pedicels, sterile flowers.*—Angle: Erect to about 30° from inflorescence axis. Strength: Strong, sturdy. Length: About 1.5 cm. Diameter: About 1 mm. Texture: Smooth, glabrous. Color: Close to 145D becoming closer to 155D with development and eventually tinged with close to 65A.

*Reproductive organs, present on fertile flowers only.*—Stamens: Quantity per flower: About five to ten. Anther shape: Round. Anther length: About 0.5 mm. Anther color: Close to 145D. Pollen amount: Scarce. Pollen color: Close to 145D. Pistils: Pistil quantity per flower: One. Pistil length: About 0.5 mm. Stigma shape: Two to three-lobed. Stigma color: Close to 146C. Style length: About 0.5 mm. Style color: Close to 146C. Ovary color: Close to 146C.

*Seeds*.—Quantity per inflorescence: Numerous. Size: Less than 0.1 mm by less than 0.1 mm. Color: Brown.

Disease & pest resistance: Plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind; to be resistant to sun scald; and to tolerate temperatures ranging from about −32° C. to about 36° C.

It is claimed:

1. A new and distinct *Hydrangea* plant named 'SMHPZ-IND' as illustrated and described.

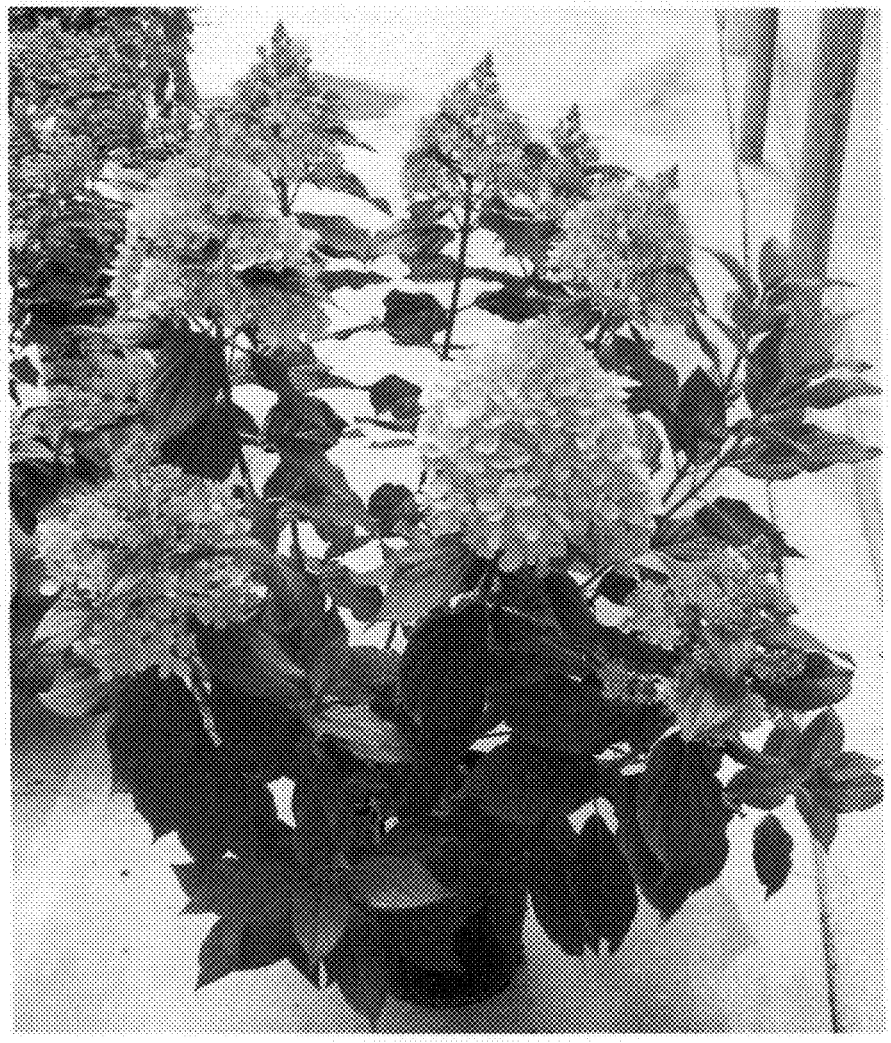

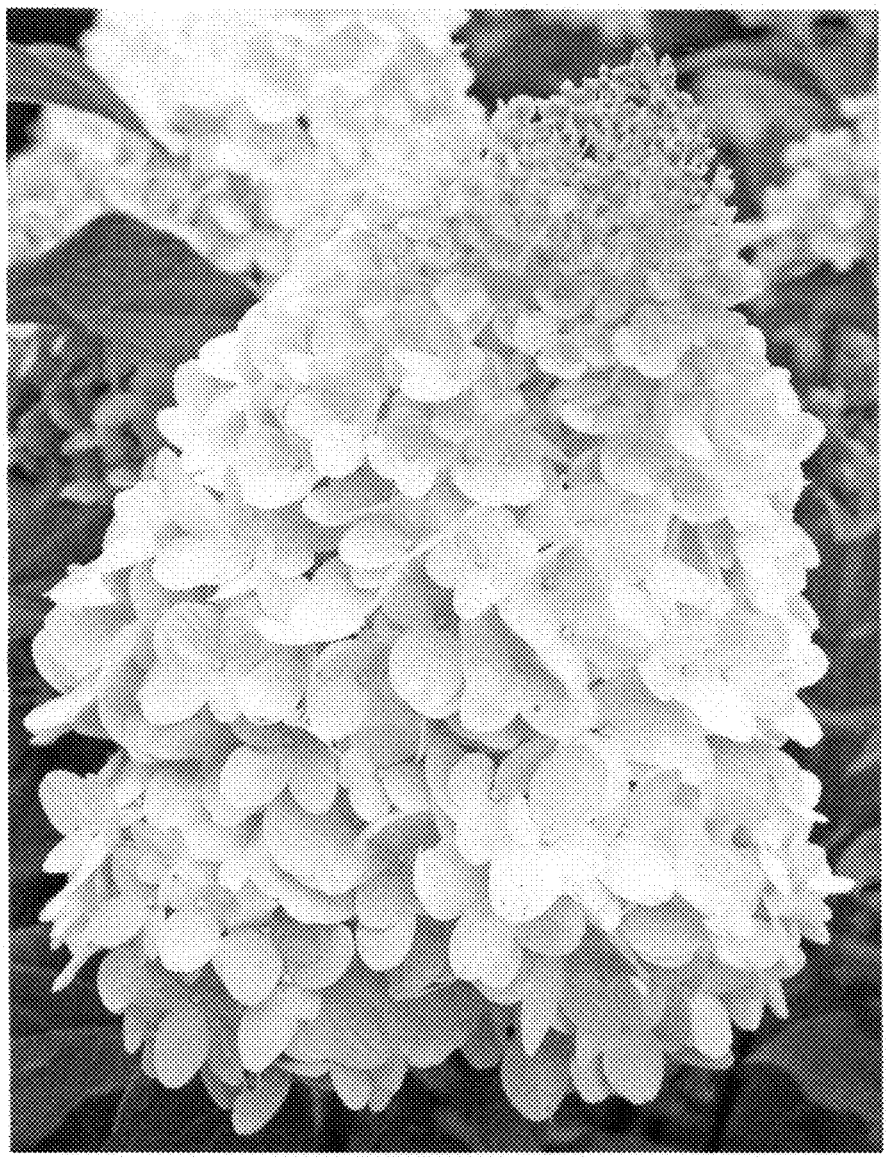

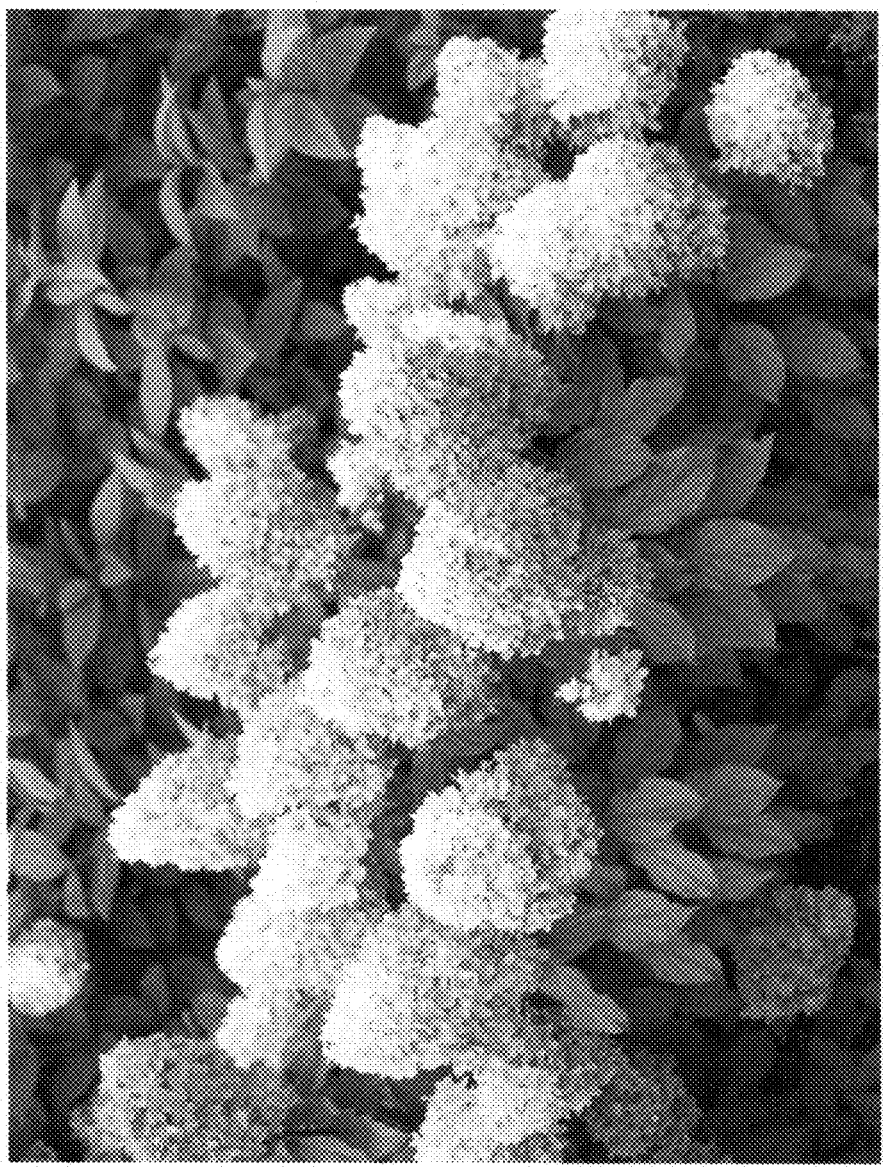

* * * * *